（12）United States Patent
Hirano et al.

(10) Patent No.: US 6,169,083 B1
(45) Date of Patent: Jan. 2, 2001

(54) PREVENTIVES/REMEDIES FOR STOMATITIS

(75) Inventors: Masaaki Hirano; Shirou Katayama, both of Tokyo (JP)

(73) Assignees: Zeria Pharmaceutical Co., Ltd., Tokyo; Hamari Chemicals Co., Ltd., Osaka, both of (JP)

( * ) Notice: Under 35 U.S.C. 154(b), the term of this patent shall be extended for 0 days.

(21) Appl. No.: 09/214,263
(22) PCT Filed: Jun. 25, 1997
(86) PCT No.: PCT/JP97/02192
 § 371 Date: Dec. 31, 1998
 § 102(e) Date: Dec. 31, 1998
(87) PCT Pub. No.: WO98/01146
 PCT Pub. Date: Jan. 15, 1998

(30) Foreign Application Priority Data

Jul. 3, 1996 (JP) .................................................. 8-191640

(51) Int. Cl.⁷ ................................................ A61K 31/555
(52) U.S. Cl. ................................ 514/184; 424/54; 514/58
(58) Field of Search ............................... 424/54; 514/184, 514/54

(56) References Cited

U.S. PATENT DOCUMENTS 4,927,817 * 5/1990 Inagaki et al. ........................ 514/184
4,981,846 * 1/1991 Matsukura et al. .................. 514/184

FOREIGN PATENT DOCUMENTS 63-229058 * 9/1988 (JP) .
8-505140 * 6/1996 (JP) .

OTHER PUBLICATIONS

Chemical Abstract 112:18319, "Reparative Effect of Sodium Alginate (Alloid AG) on Radiation Stomatitis", Aug. 1989.
Chemical Abstract 95:35654, "Pharmacologic Studies of Sodium Alginate", May 1981.

* cited by examiner

Primary Examiner—Frederick Krass
(74) Attorney, Agent, or Firm—Oblon, Spivak, McClelland, Maier & Neustadt, P.C.

(57) ABSTRACT

The invention relates to agents for treating and preventing stomatitis, comprising an L-carnosine zinc salt or L-carnosine-zinc complex, or such a compound and sodium alginate.

The agents are excellent in therapeutic and preventive effects on stomatitis and particularly exhibit marked effects on stomatitis caused by chemotherapy or radiotherapy for cancer.

6 Claims, No Drawings

PREVENTIVES/REMEDIES FOR STOMATITIS

This application is a 371 of PCT/JP97/02192, filed Jun. 25, 1997.

TECHNICAL FIELD

The present invention relates to agents for treating and preventing stomatitis.

BACKGROUND ART

Stomatitis is caused on the basis of inflammation of an intraoral mucosa and means a symptom such as erosion, erythema or ulcer arising on an intraoral mucosa, angulus oris and/or labia oris. When the stomatitis becomes severe, it is accompanied by a pain and bleeding and gives a patient such serious problems that ingestion becomes difficult.

As causes attacked by stomatitis, severe diseases, dystrophy, infection with herpes simplex virus and the like have been well known. However, the mechanism of the attack has not been yet known.

It has also been known that severe stomatitis is induced by chemotherapy and radiotherapy for cancer as a side effect thereof. The stomatitis is one of dose limiting factors upon the administration of anticancer agent. In particular, the stomatitis often obliges the radiotherapy to stop the treatment or change the therapeutic scheme.

In general, intraoral cleaning, administration of various vitamin preparations, and the like have heretofore been conducted for treating stomatitis. In order to treat stomatitis attendant on chemotherapy and/or radiotherapy for cancer, it has also been conducted to administer a mouth wash containing allopurinol or sodium alginate [Archives of Practical Pharmacy, Vol. 55, No. 1, p. 28 (1995); Japanese Journal of Hospital Pharmacy, Vol. 18, No. 5, p. 510 (1992); Japanese Journal of Nursing Acts, Vol. 37, No. 15, p. 44 (1991); The Journal of Japan Society for Cancer Therapy, Vol. 25, No. 6, p. 1129 (1990); Japanese Journal of Cancer and Chemotherapy, Vol. 16, No. 10, p. 3449 (1989); and Nippon Acta Radiologica, Vol. 49, No. 8, p. 1047 (1989)].

However, the conventional therapies for stomatitis have involved such many problems as their improving effects on the symptoms are weak, and so the effects are insufficient for severe stomatitis, and it takes a long time to improve the symptoms.

Accordingly, there has been a demand for development of an agent which is excellent in therapeutic effect and capable of achieving treatment for a short period of time.

DISCLOSURE OF THE INVENTION

The present inventors have carried out an extensive investigation with a view toward solving the above-described problems. As a result, it has been found that an L-carnosine zinc salt or L-carnosine-zinc complex, or a combination of such a compound with sodium alginate is effective for the treatment and prevention of stomatitis, and particularly has marked therapeutic and preventive effects on stomatitis caused by chemotherapy and/or radiotherapy for cancer as a side effect thereof, thus leading to completion of the present invention.

According to the present invention, there is thus provided an agent for treating and preventing stomatitis, comprising an L-carnosine zinc salt or L-carnosine-zinc complex as an active ingredient.

According to the present invention, there is also provided an agent for treating and preventing stomatitis, comprising an L-carnosine zinc salt or L-carnosine-zinc complex, and sodium alginate.

According to the present invention, there is further provided a method of treating stomatitis, which comprises administering an effective amount of an L-carnosine zinc salt or L-carnosine-zinc complex.

According to the present invention, there is still further provided a method of treating stomatitis, which comprises administering effective amounts of any one of an L-carnosine zinc salt and an L-carnosine-zinc complex, and sodium alginate.

According to the present invention, there is yet still further provided use of an L-carnosine zinc salt or L-carnosine-zinc complex for the preparation of an agent for treating and preventing stomatitis.

According to the present invention, there is yet still further provided use of any one of an L-carnosine zinc salt and an L-carnosine-zinc complex, and sodium alginate for the preparation of an agent for treating and preventing stomatitis.

BEST MODE FOR CARRYING OUT THE INVENTION

The L-carnosine zinc salt or L-carnosine-zinc complex (hereinafter referred to as zinc L-carnosine), which is an active ingredient for the agents for treating and preventing stomatitis according to the present invention, is a salt or complex composed of L-carnosine and zinc. It has been known that two types of amorphous and crystalline forms exist in such a salt or complex (Japanese Patent Publication Nos. 5367/1991 and 116160/1995). A crystalline L-carnosine-zinc complex (the international general name: "polaprezinc") is commercially available as an agent for treating gastric ulcer and is generally used in clinical treatment therefor.

Besides the anti-peptic ulcer effect (Japanese Patent Publication Nos. 5367/1991 and 116160/1995), preventive and therapeutic effects on hepatopathy (Japanese Patent Publication No. 62299/1992), therapeutic effect on pancreatitis (Japanese Patent Application Laid-Open No. 17022/1991), osteogenesis-facilitating effect (Japanese Patent Application Laid-Open No. 120257/1991), preventive and therapeutic effects on inflammatory bowel diseases (Japanese Patent Application Laid-Open No. 69338/1992), etc. have been known as the pharmacological effects of zinc L-carnosine. However, nothing has been known about the therapeutic and preventive effect of zinc L-carnosine on stomatitis.

On the other hand, sodium alginate is a polysaccharide constituting cell membranes of brown algae, and is commercially available and in common use in various preparation forms as an agent for protecting a mucosa and homostasis.

However, nothing has been known about the fact that sodium alginate exhibits therapeutic and preventive effects on stomatitis by using it in combination with zinc L-carnosine.

The zinc L-carnosine useful in the practice of the present invention may be either amorphous or crystalline. Crystalline zinc L-carnosine and amorphous zinc L-carnosine can be prepared in accordance with the processes described in Japanese Patent Publication No. 116160/1995 and Japanese Patent Publication No. 5367/1991, respectively.

The sodium alginate used in the present invention may also be a marketed product.

The agents for treating and preventing stomatitis according to the present invention are preferably provided in the preparation form of a mouth wash or intraoral ointment.

These preparations can be formulated by suitably selecting in combination proper additives from, for example, distilled water for injection, purified water, calcium carboxymethyl cellulose, sodium carboxymethyl cellulose, lactose, sorbit, mannit, sucrose, corn starch, crystalline cellulose, lactitol, cellulose derivatives, gum arabic, tragacanth gum, gelatin, polysorbate 80, talc, magnesium stearate, water, ethanol, white petrolatum, glycerol, fat, fatty oils, glycols, higher alcohols such as stearyl alcohol, plastibase, paraffin, beeswax, polyoxyethylene hydrogenated castor oil, saccharin, pine syrup, etc.

The mouth wash preparation is preferably used in the form of, for example, a suspension, syrup or emulsion. However, it is more preferably used in the form of the suspension because zinc L-carnosine is hardly soluble in water. Such a suspension may also be prepared just before use by formulating a tablet, powder or granule preparation from active ingredients in advance, grinding it in a mortar or by a grinder, adding the ground product to distilled water for injection or purified water and then optionally adding an excipient such as calcium carboxymethyl cellulose or sodium carboxymethyl cellulose thereto. The suspension may also be prepared for use by preparing an aqueous solution of sodium alginate in advance and adding and incorporating zinc L-carnosine into the aqueous solution.

In a clinical treatment, a commercially available polaprezinc preparation (trade name: "Promac Granule 15%") may also be used to prepare a suspension just before use like the above powder or granule preparation. Besides, a commercially available liquid preparation of sodium alginate is used in place of the distilled water for injection or purified water to prepare a suspension just before use, whereby the suspension may be used in the administration of zinc L-carnosine and sodium alginate in combination.

Among the agents for treating and preventing stomatitis according to the present invention, the intraoral ointment preparation can be prepared by suitably selecting in combination proper additives from plastibase, white petrolatum, paraffin, polyoxyethylene hydrogenated castor oil, beeswax, stearyl alcohol and the like, and heating and melting them to mix. The intraoral ointment preparation is preferably used for stomatitis arising on an angulus oris and/or labia oris with more effect.

When zinc L-carnosine and sodium alginate are used in combination, both components may be mixed into a preparation, or both components may be formulated into separate preparations to use them in combination at the same time. There is no difference in effect between both cases.

Although two types of amorphous and crystalline forms exist in zinc L-carnosine, there is no difference in therapeutic and preventive effects on stomatitis between them.

The dose of zinc L-carnosine varies according to the age, weight and morbid state of a patient to be administered, its therapeutic effect, an administration method, administration time, the number of times of administration, and an administration period. When only zinc L-carnosine is administered, however, it is preferred that it should be administered 1 to 10 times a day in a dose of 1 to 150 mg per once, preferably, 2 to 6 times a day in a dose of 5 to 30 mg per once.

When zinc L-carnosine and sodium alginate are used in combination, it is preferred that sodium alginate should be administered in a dose of 25 to 500 mg, preferably 50 to 300 mg per once together with the above-described dose of zinc L-carnosine.

The agents for treating and preventing stomatitis according to the present invention are effective for stomatitis by any cause of attack, but exhibit an excellent effect on stomatitis caused by chemotherapy and radiotherapy for cancer. Examples of anticancer agents used in the cancer chemotherapy include generally used agents such as 5-FU, cisplatin, methotrexate, cyclophosphamide, cytarabine, vincristine, adriamycin and mytomycin C.

The mouth wash preparation may be either swallowed or spat out after keeping it in a mouth to rinse the mouth. When stomatitis arisen on an angulus oris and/or labia oris is treated, the intraoral ointment preparation may be used, or otherwise the mouth wash preparation may be held on a swab, absorbent cotton or filmy membrane to apply it.

EXAMPLES

The present invention will hereinafter be described in more detail by the following Examples (Clinical Examples, Formulation Examples, etc.). However, the present invention is not limited to these examples. A production process of a crystalline L-carnosine zinc salt used in the Examples (Clinical Examples and Formulation Examples) and a preparation process of a 5% sodium alginate solution used therein will be described as Referential Examples.

Referential Example 1

Production Process of Crystalline L-carnosine Zinc Salt:

Sodium hydroxide (3.51 g) was dissolved in methanol (100 ml), and L-carnosine (9.96 g) was added to the solution to prepare a uniform solution. A solution with zinc acetate dihydrate (9.67 g) dissolved in methanol (145 ml) was added dropwise over 30 minutes to the uniform solution. As a result, white precipitate was gradually formed. After completion of the addition, the mixture was stirred for 2 hours, left to stand overnight and then filtered. The resultant filter cake was then washed with water (140 ml) and air-dried at 80° C. for 5 hours to obtain a crystalline L-carnosine zinc salt (12.4 g) as white powdery crystals.

Referential Example 2

Preparation Process of 5% Sodium Alginate Solution:

Sodium alginate (5 g; product of Wako Pure Chemical Industries, Ltd.) was added to purified water (100 ml), and the mixture was stirred until sodium alginate was dissolved, thereby preparing a 5% sodium alginate solution.

Examples (Clinical Examples):

The frequency indicated in each example indicates a symptomatic process and was judged on the basis of the side effect standard by the Japanese Cancer Association. The frequency and symptom thereof are as follows, and a higher frequency indicates a severer symptom.

| Frequency | Symptom |
|---|---|
| 0: | None |
| 1: | Pain and erythema |
| 2: | Erosion and ulcer |
| 3: | Ulcer, capable of ingesting only a liquid diet |
| 4: | Ulcer, accompanied by bleeding. |

Example 1

A breast cancer patient being subjected to chemotherapy; woman aged 55 years:

The patient, in the oral cavity of which erosion and ulcer had arisen (frequency 2), was got to rinse her mouse with a suspension (5 ml) obtained by mixing the crystalline L-carnosine zinc salt (150 mg), distilled water for injection (100 ml) and sodium carboxymethyl cellulose (1 g) and stirring the mixture by a mixer, and then to swallow it. This process was repeated 5 or 6 times a day. The administration was continuously conducted for 8 days. As a result, the erosion and ulcer arisen on the intraoral mucosa were completely healed (frequency 0).

Example 2

An esophageal cancer patient being subjected to chemotherapy; woman aged 57 years:

The patient, on the intraoral mucosa and angulus oris of which ulcer had arise, and who had ingested only a liquid diet (frequency 3), was got to rinse her mouse with a suspension (5 ml) obtained by mixing the crystalline L-carnosine zinc salt (450 mg), distilled water for injection (100 ml), sodium carboxymethyl cellulose (1 g) and pine syrup (small amount) and stirring the mixture by a mixer, and then to spit it out. This agent was administered 2 to 4 times a day continuously for 6 days. Thereafter, the amount of an anticancer agent was increased for 2 days. As a result, the above symptom was worsened. Accordingly, the same administration as described above was conducted for 3 days, and the agent was applied to the angulus oris with a swab for additional 2 days. As a result, the ulcer arisen on the intraoral mucosa and angulus oris was completely healed, and the patient became able to ingest a solid diet (frequency 0).

Example 3

An acute myelocytic leukemia patient being subjected to chemotherapy; woman aged 54 years:

The patient, on the intraoral mucosa of which ulcer had arise, and who had ingested only a liquid diet (frequency 3), was got to rinse her mouse with a suspension (5 ml) obtained by mixing the crystalline L-carnosine zinc salt (300 mg), purified water (100 ml) and sodium carboxymethyl cellulose (1 g) and stirring the mixture by a mixer, and then to swallow it. This process was repeated twice a day. The administration was continuously conducted for 10 days. As a result, the ulcer arisen on the intraoral mucosa was completely healed, and the patient became able to ingest a solid diet (frequency 0).

Example 4

An acute myelocytic leukemia patient being subjected to chemotherapy; man aged 24 years:

The patient, who had been difficult to speak because stomatitis had arisen on both molar gingival sides and sides of his tongue (frequency 1), was got to rinse his mouse with a suspension (5 ml) obtained by adding the crystalline L-carnosine zinc salt (150 mg) to the 5% sodium alginate solution (100 ml) and stirring the mixture by a mixer, and then to swallow it. This process was repeated 5 or 6 times a day. On the next day the treatment had been started, pain was relieved and the patient became able to speak without difficulty. After the administration was continuously conducted for 11 days, the stomatitis was completely healed (frequency 0).

Example 5

A postoperative patient of gastric cancer being subjected to chemotherapy; man aged 65 years:

The patient, on the angulus oris and labia oris of which erosion and ulcer had arisen (frequency 2), was got to rinse his mouse with a suspension (5 ml) obtained by grinding allopurinol (100 mg) in a mortar, adding the 5% sodium alginate solution (100 ml) to the ground product and then stirring the mixture by a mixer, and then to swallow it. This process was repeated 3 times a day for 9 days. However, pain was not removed (frequency 1). Thus, the patient was got to rinse his mouth with a suspension (5 ml) obtained by adding the crystalline L-carnosine zinc salt (150 mg) to the 5% sodium alginate solution (100 ml) and stirring the mixture by a mixer, and then to swallow it. This process was repeated 3 times a day for 7 days. As a result, the erosion and ulcer arisen on the angulus oris and labia oris were completely healed, and at the same time pain was banished (frequency 0).

Example 6

A breast cancer patient being subjected to chemotherapy; woman aged 46 years:

The patient, in the oral cavity of which blister had arisen (frequency 2), was got to rinse her mouse with a suspension (5 ml) obtained by mixing allopurinol (100 mg) with the 5% sodium alginate solution (100 ml) 5 times a day, and then to swallow it. This treatment was conducted for 8 days. However, the symptom was not improved. Thus, the patient was got to rinse her mouth with a suspension (5 ml) obtained by adding the crystalline L-carnosine zinc salt (150 mg) to the 5% sodium alginate solution (100 ml) and stirring the mixture by a mixer, and then to swallow it. This process was repeated 5 times a day for 5 days. As a result, the blister in the oral cavity completely disappeared (frequency 0).

Example 7

An esophageal cancer patient being subjected to chemotherapy; man aged 65 years:

The patient, in the oral cavity of which ulcer accompanied by bleeding had arisen (frequency 4), was got to rinse his mouse with a suspension (5 ml) obtained by adding the crystalline L-carnosine zinc salt (150 mg) and sodium alginate (5 g) to purified water (100 ml) and stirring the mixture by a mixer, and then to swallow it. This process was repeated 5 times a day for 11 days. As a result, the bleeding was stopped, and the ulcer was completely healed (frequency 0).

Example 8

A rectum cancer patient being subjected to both radiotherapy and chemotherapy; man aged 81 years:

A proper amount of a suspension obtained by adding the crystalline L-carnosine zinc salt (150 mg) to the 5% sodium alginate solution (100 ml) and stirring the mixture by a mixer was soaked into a swab to apply the suspension to the affected part of the patient who had suffered from angular bleeding (frequency 2). This process was repeated 5 or 6 times a day for 3 days. As a result, the angular bleeding was completely stopped (frequency 0).

Example 9

An acute leukemia patient being subjected to chemotherapy; woman aged 25 years:

The patient, on the angulus oris and labia oris of which erosion and ulcer had arisen (frequency 2), was got to rinse her mouse with a suspension (5 ml) obtained by grinding 1 g (containing 150 mg of polaprezinc) of "Promac Granule 15%" (product of ZERIA PHARMACEUTICAL CO., LTD.) in a mortar, adding the ground product to an Alloid G solution (100 ml) (5% sodium alginate solution; product of Kyosei Seiyaku K.K. and KAIGEN CO., LTD.) and then stirring the mixture by a mixer, and then to spit it out. This process was repeated 3 times a day for 37 days. As a result, the erosion and ulcer arisen on the angulus oris and labia oris were completely healed (frequency 0).

Example 10

A breast cancer patient being subjected to chemotherapy; woman aged 61 years:

The patient, on the angulus oris and labia oris of which erosion and ulcer had arisen (frequency 2), was got to rinse her mouse with a suspension (5 ml) obtained by adding the crystalline L-carnosine zinc salt (150 mg) to the 5% sodium alginate solution (100 ml) and stirring the mixture by a mixer, and then to spit it out. This process was repeated 3 times a day for 10 days. As a result, the erosion and ulcer arisen on the angulus oris and labia oris were almost banished (frequency 1).

Example 11

A rectum cancer patient being subjected to radiotherapy; man:

The patient, on the angulus oris and in the oral cavity of which ulcer accompanied by bleeding had arisen (frequency 4), was got to rinse his mouse with a suspension (5 ml) obtained by adding the crystalline L-carnosine zinc salt (150 mg) to the 5% sodium alginate solution (100 ml) and stirring the mixture by a mixer, and then to spit it out. This process was repeated 3 times a day for 17 days. As a result, the ulcer and bleeding on the angulus oris and in the oral cavity were completely healed (frequency 0).

Example 12

An esophageal cancer patient being subjected to chemotherapy; man aged 64 years:

A proper amount of an ointment obtained by adding and incorporating the crystalline L-carnosine zinc salt (150 mg) into plastibase (100 g) was held on a swab to apply it to the affected part of the patient, on the angulus oris and labia oris of which ulcer had arise, and who had ingested only a liquid diet (frequency 3). This process was repeated 3 to 5 times a day for 9 days. As a result, the ulcer in the oral cavity was completely healed, and the patient became able to ingest a solid diet (frequency 0).

Control Example: (Single administration of sodium alginate)

An esophageal cancer patient being subjected to chemotherapy; woman aged 61 years:

The patient, in the oral cavity of which erosion and ulcer had arisen (frequency 2), was got to rinse her mouse with the 5% sodium alginate solution (10 ml), and then swallow it. This process was repeated 3 to 6 times a day for 7 days. However, the ulcer was not improved at all (frequency 2).

Example 13

An esophageal cancer patient (man aged 45 years) was got to rinse his mouse with a suspension (5 ml) obtained by adding the crystalline L-carnosine zinc salt (150 mg) to the 5% sodium alginate solution (100 ml) and stirring the mixture by a mixer, and then to swallow it. After this process was conducted 5 times a day, cancer chemotherapy was started. During the cancer chemotherapy (5 days) and up to the day following the completion of the therapy, the mouth rinsing was continued 3 to 4 times a day with the same crystalline L-carnosine zinc salt-5% sodium alginate solution mixture as described above. As a result, the patient was not attacked by stomatitis at all.

Acute Toxicity:
(1) The $LD_{50}$ value of the crystalline L-carnosine zinc salt was 8,441 mg/kg as determined by oral administration to rats.
(2) The $LD_{50}$ value of the sodium alginate was 5,000 mg/kg as determined by oral administration to rats.

(Formulation Examples)

Example 14

The crystalline L-carnosine zinc salt (150 mg) was added to distilled water for injection (100 ml), and sodium carboxymethyl cellulose (1 g) was further added thereto. The resultant mixture was stirred by a mixer to obtain a suspension preparation.

Example 15

The crystalline L-carnosine zinc salt (150 mg) and sodium alginate (5 g) were added to purified water (100 ml), and sodium carboxymethyl cellulose (1 g) was further added thereto. The resultant mixture was stirred by a mixer to obtain a suspension preparation.

Example 16

The crystalline L-carnosine zinc salt (150 mg) and sodium alginate (5 g) were added to distilled water for injection (100 ml), and sodium carboxymethyl cellulose (1 g) was further added thereto. The resultant mixture was stirred by a mixer to obtain a suspension. This suspension was incorporated into white petrolatum (100 g) to obtain an intraoral ointment preparation.

Example 17

The crystalline L-carnosine zinc salt (300 mg) was added to plastibase (3 g), and the resultant mixture was mixed at ordinary temperature to obtain an intraoral ointment preparation.

INDUSTRIAL APPLICABILITY

The agents for treating and preventing stomatitis according to the present invention, which comprise zinc L-carnosine or zinc L-carnosine, and sodium alginate, have marked therapeutic and preventive effects on stomatitis, in particular, severe stomatitis caused by chemotherapy and radiotherapy for cancer. They are extremely high in safety because of their low toxicity and thus useful as agents for treating and preventing stomatitis.

What is claimed is:

1. A method of treating stomatitis, which comprises administering a stomatitis treating effective amount of an L-carnosine zinc salt or L-carnosine-zinc complex to a subject in need of such treatment.

2. A method of treating stomatitis, which comprises administering an effective amount of an L-carnosine zinc salt or an L-carnosine-zinc complex, and sodium alginate to a subject in need of such treatment.

3. The treating method according to claim 1 or 2, wherein the stomatitis is caused by chemotherapy or radiotherapy for cancer or both therapies.

4. The treating method according to claim 1 wherein administration is by mouth wash or intraoral ointment.

5. The treating method according to claim 2 wherein administration is by mouth wash or intraoral ointment.

6. The treating method according to claim 3 wherein administration is by mouth wash or intraoral ointment.

* * * * *